(12) United States Patent
Edwards et al.

(10) Patent No.: US 6,592,251 B2
(45) Date of Patent: Jul. 15, 2003

(54) CEMENT MIXING AND DISPENSING DEVICE

(75) Inventors: Brian Edwards, West Milford, NJ (US); Paul Higham, Ringwood, NJ (US); Joseph Zitelli, River Edge, NJ (US)

(73) Assignee: Howmedica Osteonics Corp., Allendale, NJ (US)

( * ) Notice: Subject to any disclaimer, the term of this patent is extended or adjusted under 35 U.S.C. 154(b) by 0 days.

(21) Appl. No.: 09/771,317

(22) Filed: Jan. 26, 2001

(65) Prior Publication Data
US 2002/0101785 A1 Aug. 1, 2002

(51) Int. Cl.[7] .............................. B01F 5/06; B01F 5/12; A61M 37/00
(52) U.S. Cl. ..................... 366/268; 336/130; 336/332; 336/334
(58) Field of Search .................. 366/268, 130, 366/332, 334, 333; 206/219; 604/82, 89, 90, 91

(56) References Cited

U.S. PATENT DOCUMENTS

| | | | | |
|---|---|---|---|---|
| 1,718,593 A | * | 6/1929 | Smith .......................... 604/413 |
| 2,477,598 A | * | 8/1949 | Hain ........................... 366/334 |
| 2,724,383 A | * | 11/1955 | Lockhart et al. ............... 604/88 |
| 2,726,656 A | * | 12/1955 | Lockhart ..................... 366/130 |
| 3,010,705 A | * | 11/1961 | Brown ........................ 366/268 |
| 3,035,820 A | * | 5/1962 | Todd et al. .................. 366/268 |
| 3,190,619 A | * | 6/1965 | Penney et al. ................. 604/82 |
| 3,610,297 A | * | 10/1971 | Raaf et al. .................... 604/89 |
| 3,700,215 A | | 10/1972 | Hardman et al. ............... 259/98 |
| 4,046,145 A | | 9/1977 | Choksi et al. ................ 128/215 |
| 4,060,082 A | | 11/1977 | Lindberg et al. ............ 128/218 |
| 4,313,440 A | | 2/1982 | Ashley ....................... 128/218 |
| 4,463,875 A | * | 8/1984 | Tepic .......................... 366/334 |
| 4,551,135 A | | 11/1985 | Gorman et al. ................ 604/82 |
| 4,743,229 A | | 5/1988 | Chu ............................ 604/82 |
| RE33,161 E | | 2/1990 | Brown et al. ................ 423/308 |
| 4,900,546 A | | 2/1990 | Posey-Dowty et al. ....... 424/81 |
| RE33,221 E | | 5/1990 | Brown et al. ................ 423/308 |
| 5,114,240 A | | 5/1992 | Kindt-Larsen et al. ....... 366/129 |
| 5,172,807 A | | 12/1992 | Dragan et al. ............... 206/219 |
| 5,248,516 A | | 9/1993 | Wheatley et al. ............... 427/3 |
| 5,276,070 A | | 1/1994 | Arroyo ........................ 523/117 |
| 5,425,580 A | * | 6/1995 | Beller ......................... 604/82 |
| 5,551,778 A | | 9/1996 | Hauke et al. ................ 366/139 |
| 5,820,632 A | | 10/1998 | Constantz et al. ............ 623/16 |
| 5,823,671 A | * | 10/1998 | Mitchell et al. ............. 366/268 |
| 5,908,054 A | | 6/1999 | Safabash et al. .............. 141/26 |
| 5,957,166 A | | 9/1999 | Safabash ...................... 141/26 |
| 6,062,722 A | * | 5/2000 | Lake .......................... 366/268 |
| 6,234,190 B1 | * | 5/2001 | Fischer et al. .............. 206/219 |
| 6,234,196 B1 | * | 5/2001 | Fischer et al. .............. 366/268 |

\* cited by examiner

Primary Examiner—Tony G. Soohoo
(74) Attorney, Agent, or Firm—Lerner, David, Littenberg, Krumholz & Mentlik, LLP (57) ABSTRACT

An apparatus and method for mixing a liquid component and a powdered component to form a bone filler has first and second syringes each having a barrel, a plunger and an exit port. The plunger is moveable with the barrel of each syringe along a longitudinal axis of the barrel. An end portion of each plunger extends beyond the end of each barrel when the plunger tip is spaced from the exit port and can be activated to move the plunger tip toward the exit port. A mechanism for mixing the liquid and powdered components is operatively connected to each of the barrels and plungers of the first and second syringes so that the relative sliding movement of first and second parts of the mechanism simultaneously moves the plungers and barrels of the first and second syringes relative to one another to move the combined liquid and powdered components back and forth between the first and second syringe.

17 Claims, 7 Drawing Sheets

CEMENT MIXING AND DISPENSING DEVICE

BACKGROUND OF THE INVENTION

The present invention relates to a method and apparatus for dispensing a setable material, such as bone cement. More particularly, it relates to a method and apparatus consisting of two syringes having their nozzles or dispensing ports interconnected so that material may be transferred back and forth from one syringe to the other.

Bone fillers and cements are widely used in dental, maxio-facial and orthopedic applications. Such cements are made by mixing a liquid and powdered component to form a paste which then sets to form a hard cement or filler.

Such a cement using calcium phosphate is described by Brown and Chow in their reissued U.S. Pat. Nos. RE 33,161 and RE 33,221 and by Constantz et al. in their U.S. Pat. No. 5,820,632. Such a cement using polymethyl methacrylate is described in U.S. Pat. Nos. 4,900,546 and 5,276,070. Mixing devices for these powder and liquid components have been the subject of numerous patents.

The use of two syringes to mix two liquid substances and then dispense the mixture from one syringe is known from U.S. Pat. No. 3,700,215 to Hardman et al. This patent illustrates the outlet nozzles of a pair of syringes connected by a coupling. A perforated mixing tube is slidably mounted within the coupling so that depressing the plunger on one syringe drives the liquid contents of that syringe through the tube into the other syringe and simultaneously drives the perforated mixing tube into the other syringe. The plunger of the other syringe is then depressed, causing the contents to be driven back into the first syringe. This process is repeated a desired number of times until the liquid substances are appropriately mixed. This mixing system is unsuitable for transferring an only partially wetted powdered and liquid component from one syringe to another.

U.S. Pat. No. 4,743,229 to Chu illustrates a pair of syringes coupled at their outlet nozzles. One of the syringes contains a fibrillar collagen which is injected into the second syringe which contains particulate mineral material. No further mixing is taught.

U.S. Pat. No. 5,908,054 to Safabash et al. relates to a pair of syringes coupled by a fluid transfer assembly. A hollow tube is mounted within the syringes and has first and second ends situated within the interiors of the syringes. The tube has openings to permit the flow of fluid to be transferred from the interior of the first syringe to the second syringe. Again, this design is unsuitable for passing a high viscosity partially mixed granular/liquid material through the tube.

U.S. Pat. No. 5,957,166 to Safabash relates to a device similar to that shown in his U.S. Pat. No. 5,908,054, with the exception that the perforated tube has a pattern of holes wherein the size and spacing is adjusted to provide an uneven fluid distribution within the second syringe. Again, such a device is unsuitable for transferring a viscous mixture from one syringe to another syringe.

U.S. Pat. No. 4,551,135 to Gorman et al. relates to a two component mixing syringe having a flared barrel to facilitate to the extrusion of the plastasized mass. U.S. Pat. No. 4,046,145 discloses a connector for use in connecting a pair of syringes.

None of the above references disclose a mechanism designed to allow a syringe containing a liquid component to be connected to a syringe containing a powdered component and allowing the liquid to be injected into the powder in the second syringe and then enabling the liquid-powder combination to be injected back into the first syringe. It has been found that the initial injection of the liquid-powder combination back into the first syringe can require more force than can be generated by simply manually depressing the plunger of the second syringe. Consequently, a mechanism has been provided to assist the individual mixing the liquid and powder components in moving the materials back and forth from one syringe to the other over a number of cycles. It has also been found that imparting mechanical energy into the mixture during mixing beyond that inputted by hand mixing increases the final strength of the set material. This is accomplished by repeating the transfer from syringe to syringe for several cycles after wetting.

SUMMARY OF THE INVENTION

A primary object of the present invention is to provide a simple and inexpensive mixing and dispensing device which will enable the mixing of a setable powder and liquid combination by assisting in the movement of the liquid stored in a first syringe into a powdered component stored in a second syringe and then moving the combination back to the first syringe and repeating the transfer over a number of cycles.

It is a further object of the invention to provide a kit containing two syringes, one containing a liquid component and the other containing a powder component which, when mixed, form a setable cement for use in filling bone defects and inducing bone healing.

It is another object of the invention to enable the end to end connection of two syringes and allowing the connected syringes to be placed in a simple mechanism which allows for the mixing of the liquid and powdered components by the repeated transfer of the liquid powder combination from one syringe to the other.

It is yet an additional object of the invention to move the mixed cement into one syringe, dissembling the two syringes and using the syringe filled with the mixed liquid and powdered components as a dispensing syringe for placing the mixed cement prior to its setting in vivo where it sets to form hard bone cement or bone filler.

These and other objects of the invention are accomplished by an apparatus for mixing a liquid component and a powdered component which includes first and second syringes, each having a barrel with an exit port at a first end and plunger moveable within the barrel along a longitudinal axis of said barrel. Activation of an outer portion of the plunger which extends beyond a second end of the barrel opposite the first end causes the plunger tip to move towards the exit port or nozzle. The first syringe contains a liquid component and the second syringe contains a powdered component. A mechanism for mixing the two components has a part operatively connected to each of the barrels and a part connected to the portion of the plunger on each syringe extending beyond the end of the barrel so that the relative sliding movement of the two mechanism parts simultaneously moves the plungers and the barrels with respect to each other.

The first part of the mechanism has contact surfaces for contacting the outer portion of the plungers extending beyond the end of each barrel and the second part contacts each barrel portion and supports the same. The first and second parts are slidably moveable with respect to one another in a direction parallel to the longitudinal axis of each barrel. Each barrel has a flange located at a predetermined distance along its length and extending from an outer surface of the barrel for contacting the second part of this mechanism in a manner which prevents axial movement of the barrel with respect to the second part. Likewise, the outer portion of the plungers are captured within the first part of the slide mechanism to prevent relative movement of the plungers with respect to the first part. To mix the cement, the second part slides with respect to the first part of the mechanism such that the plungers remain stationary with respect to the first part with the barrels being moved by the second part relative to the plungers held by the first part. A handle is provided on one of the first or second parts to enable the individual doing the mixing to generate sufficient force to move the combined liquid and powder components from one syringe to the other.

The first and second parts slide with respect to each other a distance equal to the initial distance between a tip of said plunger facing the exit port and the exit port so that the entire contents of each syringe are transferred from one syringe to the other during each cycle of mixing. In general, once all of the powder component has been wetted by the liquid component, three to five cycles of mixing have been found sufficient to completely mix the cement to a homogenous consistency.

The method for mixing the two component cement includes placing a liquid component in the barrel of a first syringe where the syringe has a moveable plunger and an exit port, both extending along a longitudinal axis of the barrel. Placing a powdered component in the barrel of a second syringe with the syringe again having a moveable plunger and an exit port both extending along a longitudinal axis of the barrel. Then connecting both exit ports of each syringe and transferring the liquid component of the first syringe of the second syringe by activating the plunger of the first syringe. Thereafter, the combined liquid and powdered components are transferred from the second syringe back to the first syringe by activating the plunger in the second syringe and repeating the back and forth transfer between the first syringe and the second syringe until the powder is completely wetted and then at least two additional times and preferably three to five. The syringes are then dissembled with the syringe containing the combined liquid and powdered component being using to dispense the mixture into the body.

While the preferred method of mixing is manual, those skilled in the art could easily develop a powered reciprocating mechanism for simultaneously moving the plungers back and forth within the barrels of the syringes.

These and other objects and advantages of the present invention will become apparent from the following description of the accompanying drawings, which disclose several embodiments of the invention. It is to be understood that the drawings are to be used for the purposes of illustration only and not as a definition of the invention.

BRIEF DESCRIPTION OF THE DRAWINGS

The invention can be performed in various ways and an embodiment will now be described by way of example and with reference to the accompanying drawings in which similar characters denote similar elements throughout the several views.

DETAILED DESCRIPTION OF THE PREFERRED EMBODIMENTS

Figure 1:
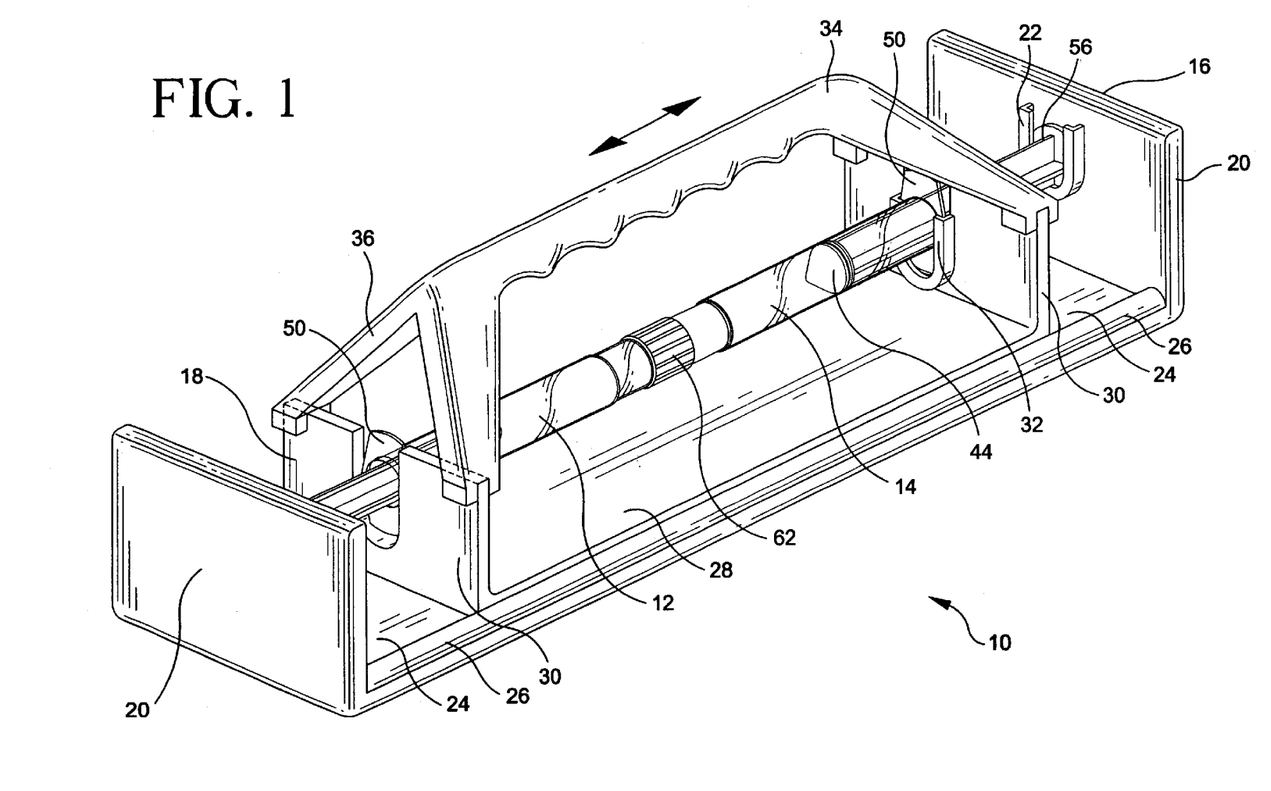
FIG. 1 shows an isometric view of the slide mechanism of the present invention supporting two syringes for mixing a liquid and a powder component.
Figure 2:
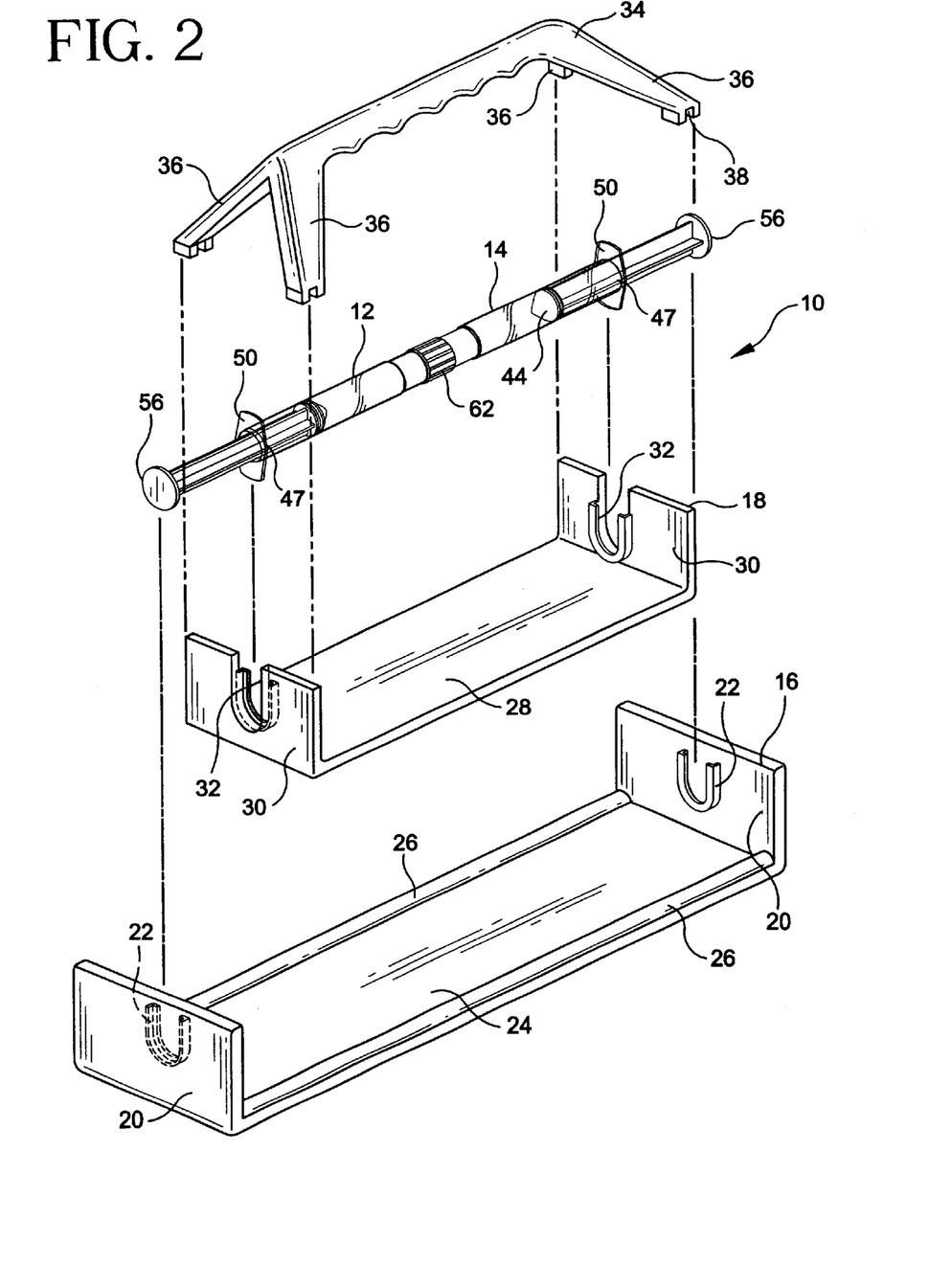
FIG. 2 is an exploded isometric view of the mechanism of FIG. 1 showing the coupled syringes prior to insertion into the slide mechanism of the present invention.

Referring to FIGS. 1 and 2 there is shown the mixing mechanism generally denoted as 10 capable of enabling the repeated transfer of the components of two syringes 12 and 14 from one syringe to the other. The mixing mechanism 10 has a first part 16 in which a second part 18 is mounted for sliding engagement. First part 16 has a pair of end walls 20 on which receptacles 22 are mounted. In the preferred embodiment, first part 16 includes a bottom surface 24 having a pair of edge rails 26.

In the preferred embodiment, second part 18 includes a base 28 and a pair of end walls 30. Base 28 is designed to fit between rails 26 of first part 16 to be guided thereby. Each end wall 30 of second part 18 includes a receptacle 32 similar to receptacle 22, the function of which will be described hereinbelow.

In the preferred embodiment, a handle 34 is adapted to engage second part 18 by means of four legs 36. In the preferred embodiment, each leg 36 includes a slot 38 which is sized to slide over and capture end walls 30 of second part 18.

Figure 3:
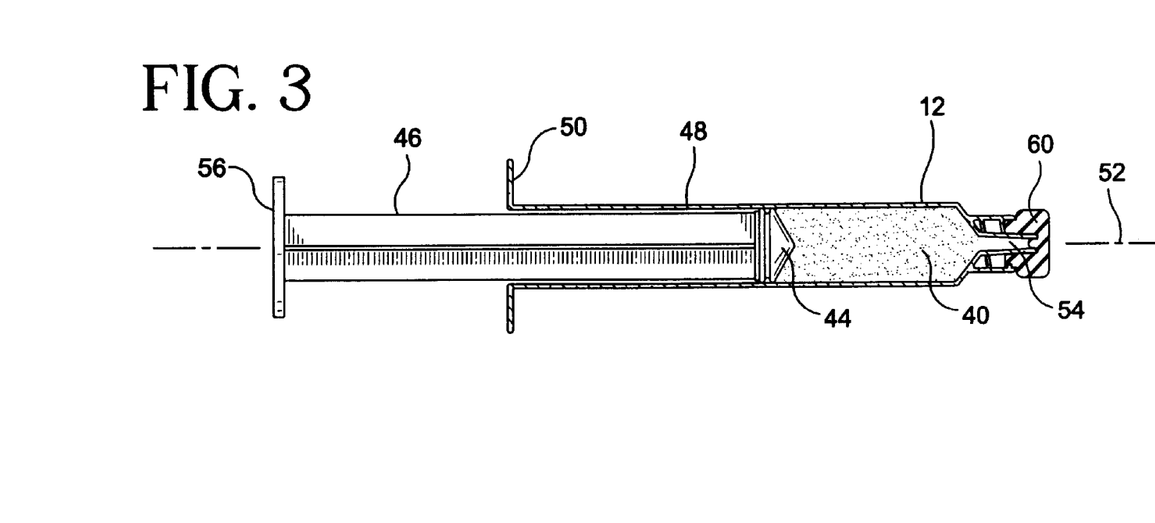
FIG. 3 and FIG. 4 are elevation views of the first and second syringes of the present invention containing a liquid component and a powder component respectively prior to being coupled.
Figure 4:
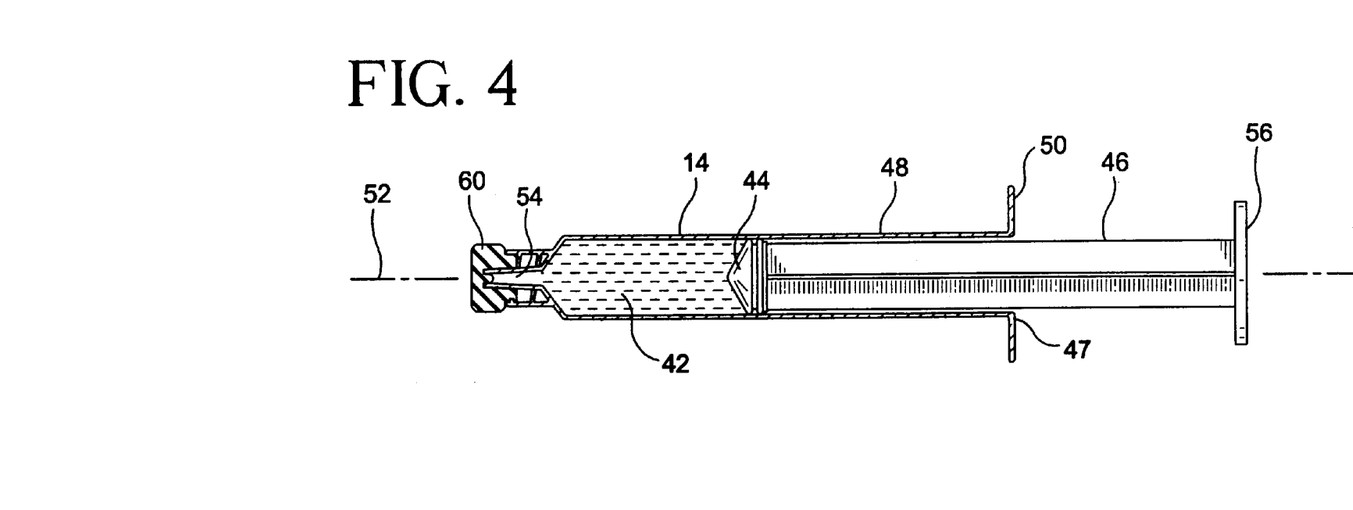

Referring to FIGS. 3 and 4, there is shown syringes 12 and 14 respectively with syringe 12 containing a powdered component 40 and syringe 14 containing a liquid component 42. Syringes 12 and 14 are normally pre-filled and provided as a kit and are connected together in the operating room when the need for a bone filler or bone cement arises. In the preferred embodiment, each syringe has a barrel 48 and a plunger 44 which has a portion 46 extending beyond the end 47 of barrel 48 of each syringe. At end 47 of barrel 48 of each syringe there is a flange 50 which extends outwardly from the outer surface of each barrel in a direction generally perpendicular to longitudinal axis 52 of each syringe. While the flanges 50 shown in FIGS. 3 and 4 are located at end 47 of each barrel 48, they could just as easily be located intermediate end 47 and exit port 54 of barrel 48. The end of each plunger portion 46 includes an end flange 56 again extending generally perpendicular to the longitudinal axis 52. Prior to use, syringes 12 and 14 include a seal 60 which seals exit port 54 and maintains the sterility of the exit port.

In the preferred embodiment, flange 50 is sized to be captured in receptacles 32 in both end walls 30 of second part 18. Likewise flanges 56 at the ends of plungers 44 are sized to be captured within receptacles 22 mounted on end walls 20 of first part 16. In the preferred embodiment, receptacles 22, 32 are generally U-shaped and made up on an L-shaped flange fixedly attached to the walls 20, 30. The thickness of the L-shape is sized to correspond to the thickness of the flanges 50, 56. Thus, flanges 50, 56 may be easily slid into the flanges in the vertical direction and prevented from horizontal movement with respect to either the first or second parts 16, 18.

As best seen in FIG. 2 syringes 12 and 14 may be connected by any well known connector 62 after the removal of the seals 60. Such connectors are well known such as a standard luer connector female to female which would accept the male exit port or nozzle 60 of each syringe 12, 14. Such luer connectors are readily available such as, for example, from Fisher Scientific.

Still referring to FIG. 2, mixing mechanism 10 is assembled by placing second part 18 within the rails 26 of first part 16. In this position, second part 18 may be slid between ends 20 of first part 16 while being guided by rails 26. The coupled syringes 12 and 14 are placed in the sliding mechanism by placing flanges 50 within receptacles 32 and flanges 56 within receptacles 22. Handle 34 is then placed over and coupled to second part 18 by placing slots 38 into engagement with the walls 30.

Figure 5:
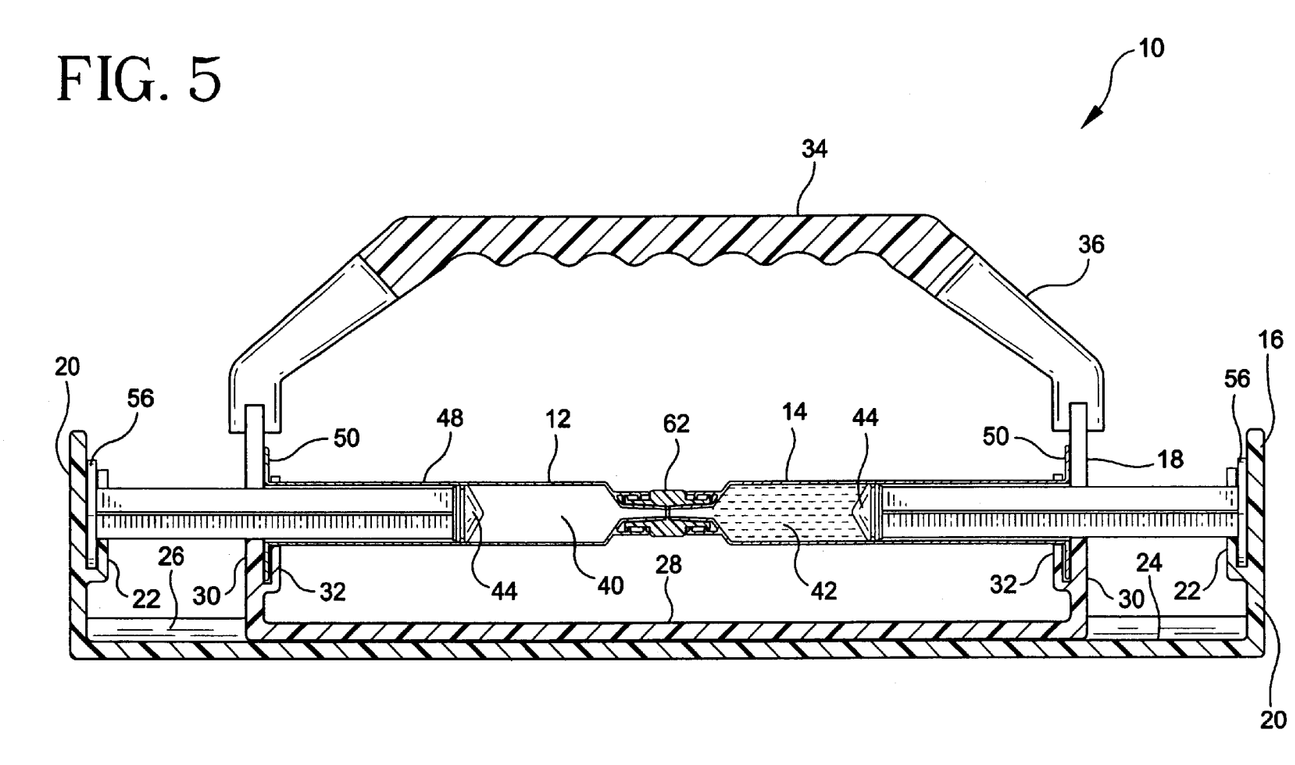
FIG. 5 is an elevation view of the coupled first and second syringes mounted in the slide mechanism of the present invention.

Referring to FIG. 5, there is shown an elevation view of the assembled mechanism containing syringes 12 and 14 prior to the mixing of powdered component 40 and liquid component 42. Prior to mixing the syringes, barrels 48 and the second part 16 are centered with respect to first part 18.

Figure 6:
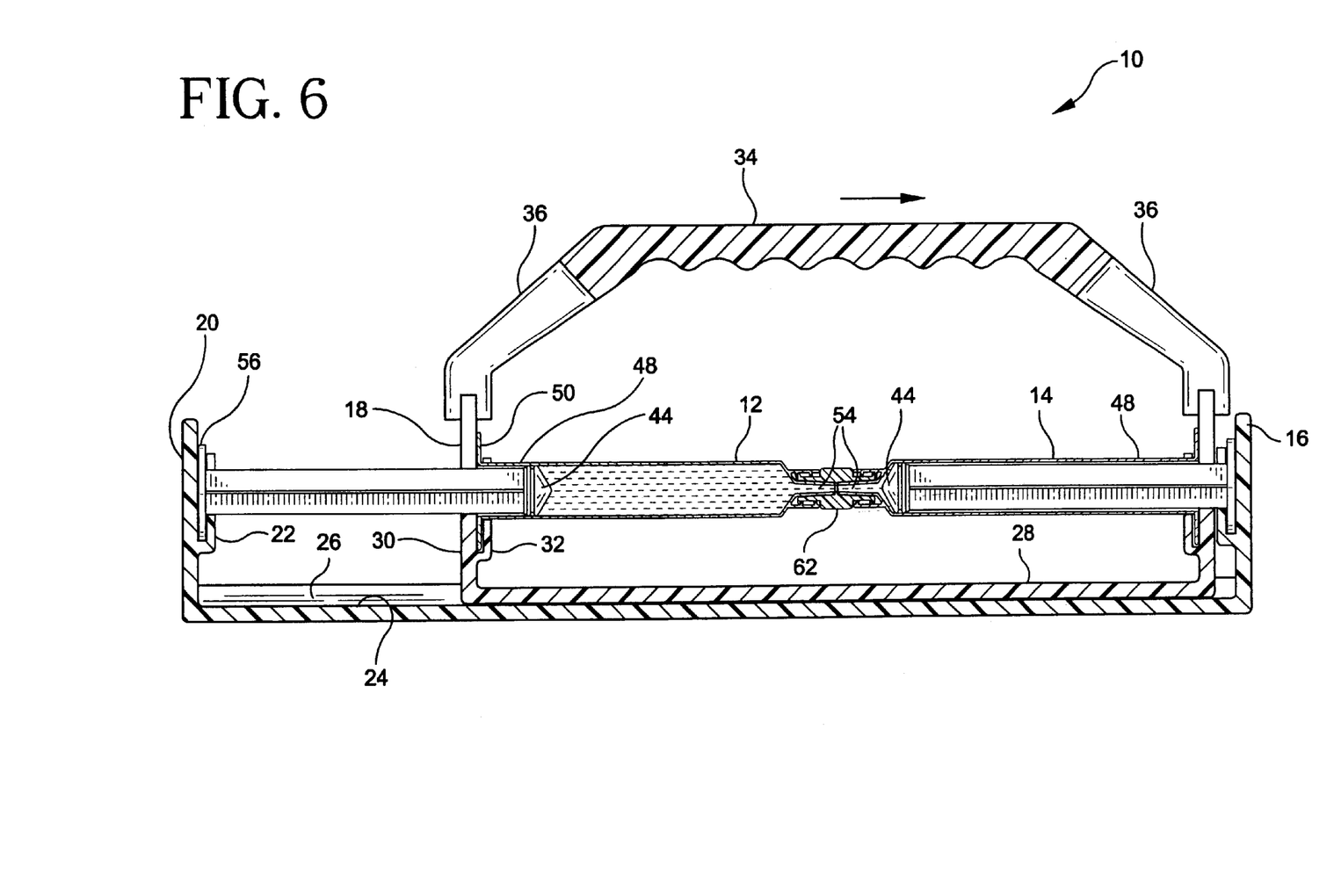
FIG. 6 is an elevation view showing the slide mechanism of the present invention with the dual syringes mounted therein in a position in which the liquid component of the right syringe has been transferred to the left syringe containing the powdered component by movement of the sliding part of the mechanism in a manner which moves the plunger of the right syringe to its exit port.

Referring to FIG. 6, there is shown an elevation view of slide mechanism 10 in the position where the liquid component of syringe 14 had been transferred into the syringe 12 with the powdered component. This is accomplished by moving or sliding second part 18 with respect to first part 16 to end wall 20 thereof towards the right of FIG. 6. As can be seen in the preferred embodiment, plungers 44 remain stationary with respect to first part 16 and barrels 48 move with second part 18 so that plunger 44 of syringe 14 moves to exit port 54 thereof. Simultaneously, plunger 44 of syringe 12 moves towards end 47 thereof opposite its exit port 54. The mechanism of course could be made so that the second part remains stationary and the first part and the plungers of each syringe simultaneously move with the movement of first part 16 while second part 18 is held stationary.

Figure 7:
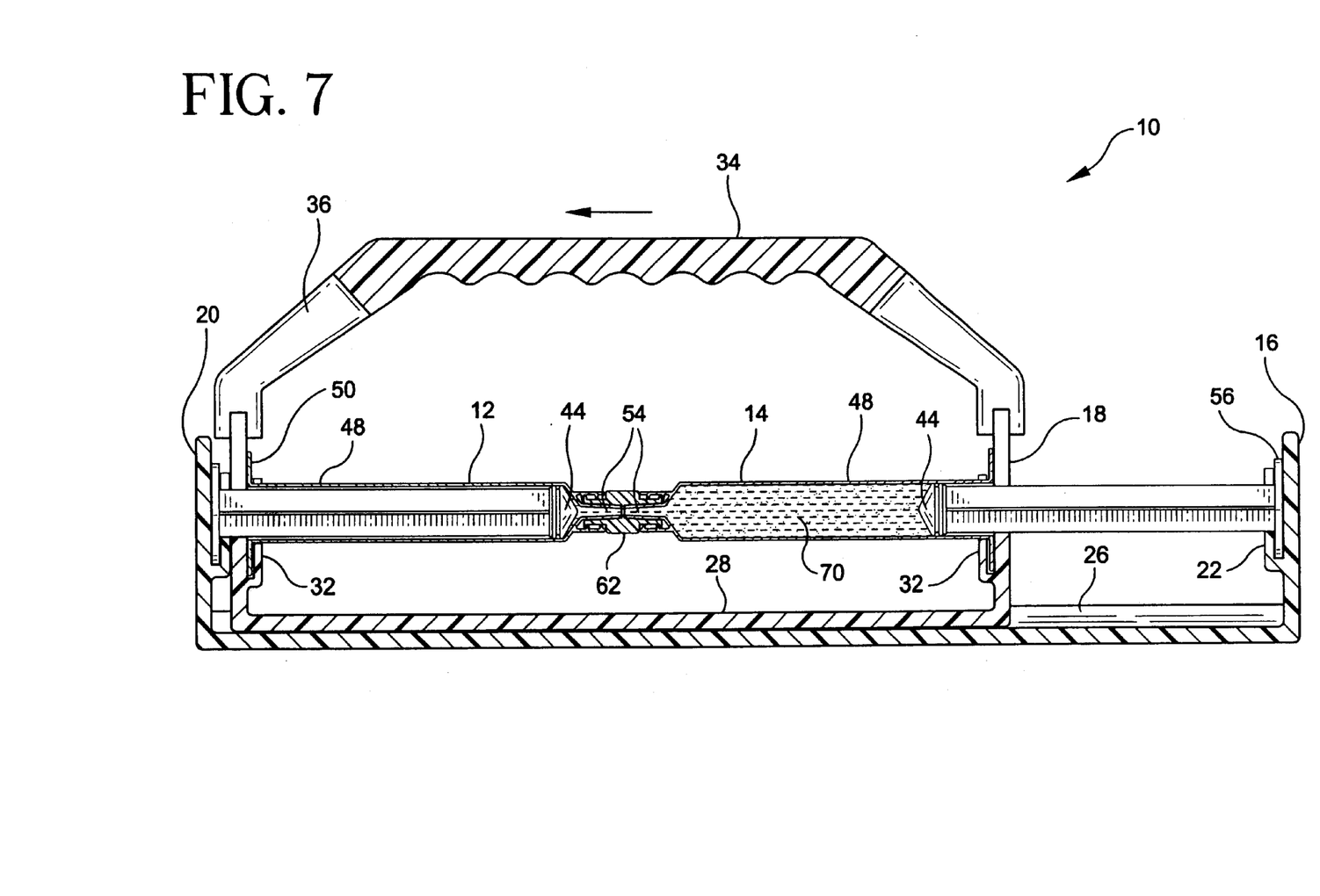
FIG. 7 is an elevation view similar to FIG. 6 in which the slide mechanism is moved to the opposite end so that the plunger of the second syringe has forced the combined liquid and powdered component back into the right syringe.

Referring FIG. 7, there is shown in elevation slide mechanism 10 of the present invention with the combined liquid and powdered material syringe 12 being forced back into syringe 14 by movement of second part 18 towards the opposite end wall 20 from that shown in FIG. 6. By moving handle 34 and second part 18 towards the left of FIG. 7, plunger 44 of syringe 12 is moved towards exit port 54 thereof, thereby transferring the liquid and powdered components from syringe 12 into syringe 14. As described above, plunger 44 of syringe 14 is moved towards the end 47 of barrel 48 opposite its exit port 54. In the preferred method, this transfer from syringe 12 to syringe 14 back to syringe 12 is repeated for three to five cycles after all of the powder component has been wetted by the liquid component. The wetting may take one or two cycles depending on the liquid to powder ratio. These cycles are accomplished by repeatedly moving handle 34 and first part 18 back and forth from the left end wall 20 to the right end wall 20 of first part 16. After this repeated transfer of materials between the syringes 12 and 14 is accomplished, either syringe 12 or 14 may be utilized to dispense the mixed liquid and powdered components.

Figure 8:
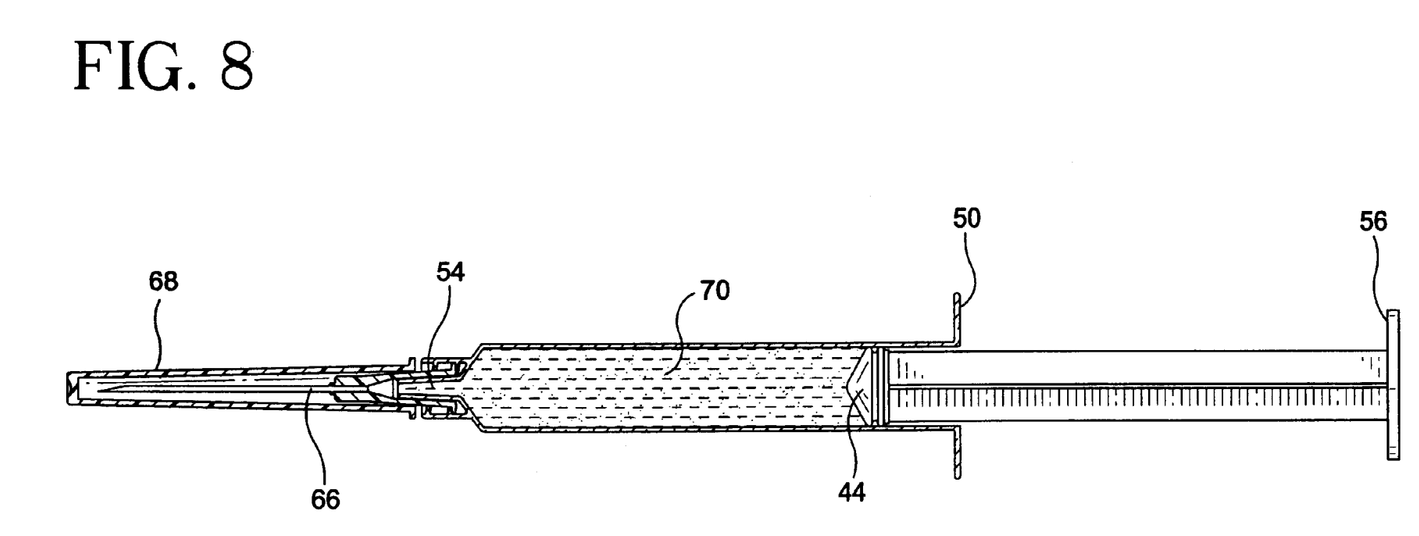
FIG. 8 is an elevation view of one of the first or second syringes containing the combined mixed powdered and liquid component ready for dispensing into the body.

Referring to FIG. 8, a standard needle 66 is attached to exit port or nozzle 54 of the selected syringe 12 or 14 and a protective cover 68 is placed thereover to protect the user. The combined material 70 may then be dispensed in a standard manner by manually moving plunger 44 towards the exit port 54 to discharge the material. A needle and protective cover combination is placed on exit port. Cover removed from discharge.

As indicated above, the powdered component can be a calcium phosphate cement, a glass ionomer cement or a powdered polymethyl methacrylate component. The liquid in the case of the calcium phosphate components can either be water or a sodium phosphate solution with the liquid in the methacrylate system being a monomer of methacrylate. Whichever cements are used, the slide mechanism 10 of the present invention allows for the complete mixing of the powder and liquid components and provides sufficient mechanical advantage to allow this to occur.

While several examples of the present invention have been described, it is obvious that many changes and modifications may be made thereunto, without departing from the spirit and scope of the invention.

Although the invention herein has been described with reference in particular to embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

What is claimed is:

1. A method for mixing a two component cement comprising:

placing a liquid component in a barrel of a first syringe, said syringe having a movable plunger and an exit port extending along a longitudinal axis of said barrel;

placing a powdered component in a barrel of a second syringe, said syringe having a moveable plunger and an exit port extending along a longitudinal axis of said barrel;

connecting the exit ports of each syringe;

mounting said syringes in a two part mechanism wherein the syringe barrels are connected to a first part and the syringe plungers in said second part;

fixing said plungers of said first and second syringes to prevent motion thereof with respect to said second part;

transferring the liquid component from the first syringe to the second syringe by moving said first part with respect to said second part; and thereafter mixing said components by transferring said combined liquid and powder components from said second syringe back to said first syringe by said movement repeating said back and forth transfer between first and second syringe at least two additional times.

2. The method as set forth in claim 1, wherein said transfer back and forth between said first and second syringes is repeated for at least five cycles.

3. The method as set forth in claim 1, wherein said longitudinal axis of said first and second syringes are connected in axial alignment.

4. The method as set forth in claim 3, wherein said transfer of liquid and powder between said syringes is accomplished by placing said connected first and second syringes in said mechanism and moving one plunger of said first and second syringe towards its corresponding exit port while simultaneously allowing the other plunger to move away from its corresponding exit port.

5. The method as set forth in claim 4, wherein said mechanism permits both of said plungers to move equal distances during said repeated transfer to the combine liquid and powder between said first and second syringes.

6. The method as set forth in claim 5, wherein the first part slides with respect to said second part a distance equal to the distance between a tip of said plunger and the first end of said syringe prior to said mixing of said liquid and powdered components.

7. The method as set forth in claim 1, wherein one of said syringes is used to dispense said mixed liquid and powdered components into the body.

8. An apparatus for mixing a liquid component and a powdered component comprising:

first and second syringes each having a barrel with an exit port at a first end and a plunger movable within said barrel along a longitudinal axis of said barrel by the activation of an outer portion of said plunger extending beyond a second end of said barrel opposite said first end said first syringe containing said liquid component and said second syringe containing said powdered component;

a mechanism having a first part operatively connected to each of said barrels and a second part contacting the portion of said plunger on each barrel extending beyond the second end of said barrel so that relative sliding movement of the first and second parts of said mechanism produces relative movement of said barrels with respect to said plungers, wherein said mechanism second part has contact surfaces for contacting said outer portion of said plungers extending beyond the second end of each barrel and said first part contacts each barrel portion for supporting the same, said first and second parts moveable with respect to one another in a direction parallel to said barrel longitudinal axis, each barrel has a flange on an outer surface thereof for contacting said first part of said mechanism in a manner to prevent axial movement of said barrel with respect to said first part, said outer portion of said plungers are captured within said second part of said mechanism and prevented from relative movement with respect thereto, said second part of said mechanism is stationary with respect to said plungers as said first part moves with respect to said second part.

9. The apparatus as set forth in claim 8, wherein said first part includes a handle portion to facilitate sliding of said first part with respect to said second part.

10. The apparatus as set forth in claim 8, wherein the first part slides with respect to said second part a distance equal to the distance between a tip of said plunger and the exit port of said syringe prior to said mixing of said liquid and powdered components.

11. An apparatus for mixing a powdered component and a liquid component comprising:

a first syringe having a barrel containing the liquid component and a moveable plunger extending along a longitudinal axis of the barrel and exit port;

a second syringe having a barrel containing a powdered component and a moveable plunger extending along a longitudinal axis of the barrel and an exit port;

a connector for connecting said exit ports together; and a means for assisting the movement of said plunger in said second syringe towards said first syringe after said liquid component has been injected therein, wherein said means for assisting includes a slide mechanism operatively connected to each of said barrels and contacting the portion of said plunger on each barrel extending beyond the end of said barrel so that sliding movement of the slide mechanism simultaneously moves said plungers in the same direction with respect to said barrels.

12. The apparatus as set forth in claim 11, wherein said slide mechanism comprises a first part having contact surfaces for contacting a surface of the portion of said plungers extending beyond the end of each barrel and a second part contacting each barrel portion for supporting the same, said first and second parts moveable with respect to one another in a direction parallel to said barrel longitudinal axies.

13. The apparatus as set forth in claim 12, wherein each barrel has an outer flange for contacting said second part of said slide mechanism in a manner to prevent axial movement of said barrel with respect to said second part.

14. The apparatus as set forth in claim 13, wherein ends of said plunger are captured within first part of said slide mechanism and prevented from relative movement within respect thereto.

15. The apparatus as set forth in claim 14, wherein said first part of said slide mechanism is stationary and said second part slides with respect to said first part.

16. The apparatus as set forth in claim 15, wherein said second part includes a handle portion to facilitate sliding of said second part with respect to said first part.

17. An apparatus for mixing a liquid component and a powdered component comprising:

first and second syringes each having a barrel with an exit port at a first end and a plunger movable within said barrel along a longitudinal axis of said barrel by the activation of an outer portion of said plunger extending beyond a second end of said barrel opposite said first end said first syringe containing said liquid component and said second syringe containing said powdered component;

a mechanism having a first part operatively connected to each of said barrels and a second part contacting the portion of said plunger on each barrel extending beyond the second end of said barrel so that relative sliding movement of the first and second parts of said mechanism produces relative movement of said barrels with respect to said plungers, each of said plungers including a flange thereon and said second part of said mechanism including receptacles for capturing said flange on each plunger and preventing movement thereof with respect to said second part.

* * * * *

UNITED STATES PATENT AND TRADEMARK OFFICE
CERTIFICATE OF CORRECTION

PATENT NO. : 6,592,251 B2
DATED : July 15, 2003
INVENTOR(S) : Brian Edwards, Paul Higham and Joseph Zitelli It is certified that error appears in the above-identified patent and that said Letters Patent is hereby corrected as shown below:

Column 3,
Line 32, "." should read -- , --.
Line 32, "The" (second occurrence) should read -- the --.
Line 43, "using" should read -- used --.

Column 4,
Line 47, "is" should read -- are --.

Column 5,
Line 49, after "Referring", insert -- to --.
Line 49, "in" should read -- an --.

Column 6,
Line 10, after "port" insert -- 54 --.
Line 59, "syringe" should read -- syringes --.

Column 7,
Line 8, "combine" should read -- combined --.
Line 25, after "end" insert -- , --.

Column 8,
Line 24, "axies" should read -- axis --.
Line 44, after "end" insert -- , --.

Signed and Sealed this

Seventh Day of October, 2003

JAMES E. ROGAN
*Director of the United States Patent and Trademark Office*